(12) United States Patent
Rossen et al.

(10) Patent No.: US 8,865,906 B2
(45) Date of Patent: Oct. 21, 2014

(54) PROCESS FOR THE PREPARATION OF A COMPOUND USEFUL AS AN INHIBITOR OF TAFIA

(75) Inventors: Kai Rossen, Frankfurt am Main (DE); Volker Kraft, Frankfurt am Main (DE); Hermut Wehlan, Frankfurt am Main (DE); Antony Bigot, Paris (FR); Veronique Crocq-Stuerga, Paris (FR)

(73) Assignee: Sanofi, Paris (FR)

( * ) Notice: Subject to any disclaimer, the term of this patent is extended or adjusted under 35 U.S.C. 154(b) by 269 days.

(21) Appl. No.: 13/319,474

(22) PCT Filed: May 11, 2010

(86) PCT No.: PCT/EP2010/056426
§ 371 (c)(1),
(2), (4) Date: May 29, 2012

(87) PCT Pub. No.: WO2010/130718
PCT Pub. Date: Nov. 18, 2010

(65) Prior Publication Data
US 2012/0245358 A1 Sep. 27, 2012

(30) Foreign Application Priority Data
May 15, 2009 (EP) ..................................... 09290366

(51) Int. Cl.
C07D 401/06 (2006.01)
C07D 233/84 (2006.01)
C07D 233/64 (2006.01)

(52) U.S. Cl.
CPC ............ *C07D 233/64* (2013.01); *C07D 401/06* (2013.01); *C07D 233/84* (2013.01)
USPC ...................................................... 546/272.7

(58) Field of Classification Search
USPC ...................................................... 546/272.7
See application file for complete search history.

(56) References Cited

U.S. PATENT DOCUMENTS

2007/0129341 A1    6/2007 Kallus et al.

FOREIGN PATENT DOCUMENTS

CA            2 563 401 A1    11/2005

OTHER PUBLICATIONS

Dorwald , Side Reactions in Organic Synthesis, 2005, Wiley: VCH Weinheim Preface, pp. 1-15 & Chapter 8, pp. 279-308.*
Bouma, B.N. et al., "Thrombin-activatable fibrinolysis inhibitor (TAFI, plasma, procarboxypeptidase B, procarboxypeptidase R, procarboxypeptidase U)," Journal of Thrombosis and Haemostasis (2003), vol. 1, pp. 1566-1574.
Greene, T.H. et al., "Protection for the Amino Group," Protective Groups in Organic Synthesis (1999), pp. 502-537.
Greene, Theodora W. et al., "Protection for the Amino Group," Protective Groups in Organic Synthesis, Third Edition (1999), pp, 494-653.
Han, W.C. et al., "Regiospecific cleavage of strained tri- and tetraquinane .beta.-diketones via retro-claisen reaction," Journal of the American Chemical Society (1982), vol. 104, No. 1, pp. 318-321.
Satoh, Koji et al., "An efficient synthesis of a key intermediate of DU-6859a via Asymmetric Microbial Reduction," Chemical and Pharmaceutical Bulletin (1998), vol. 46, No. 4, pp. 587-590.
Bajzar, Laszio, "Thrombin Activatable Fibrinolysis Inhibitor and an Antifibrinolytic Pathway," Arteriosclerosis, Thrombosis and Vascular Biology (2000), vol. 20, pp. 2511-2518.
Marckwald, W., Chem. Ber. (1982), vol. 25, pp. 2354-2373.
Wislicenus, Wilhelm, Chem. Ber. (1886), vol. 19, pp. 3225-3228.
Wislicenus, Wilhelm, Chem. Ber. (1891), vol. 24, pp. 1257-1263.
Xi, Ning et al., "Regio-controlled synthesis of N-substituted imidazoles," Tetrahedron Letters (2005), vol. 46, pp. 7315-7319.
International Search Report dated Jul. 15, 2010 issued in PCT/EP2010/056426.
International Preliminary Report on Patentability dated Nov. 15, 2011 issued in PCT/EP2010/056426.

* cited by examiner

*Primary Examiner* — Patricia L Morris
(74) *Attorney, Agent, or Firm* — Scully, Scott, Murphy & Presser, P.C.

(57) ABSTRACT

The present invention relates to a process for the preparation of a compound of the formula I,

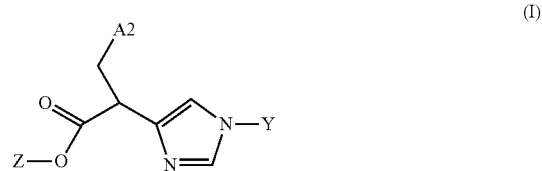

which comprises reacting a compound of the formula IV

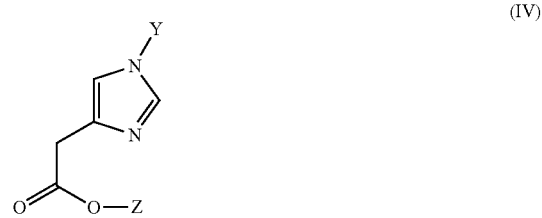

with an oxalic acid diester and to novel intermediate compounds used therein.

25 Claims, No Drawings

PROCESS FOR THE PREPARATION OF A COMPOUND USEFUL AS AN INHIBITOR OF TAFIA

BACKGROUND OF THE INVENTION

The present invention relates to a process for the preparation of a compound of the formula I, which inhibit the enzyme TAFIa (activated thrombin-activatable fibrinolysis inhibitor), and to the novel intermediate compounds used therein.

The enzyme TAFIa is produced for example through thrombin activation from the thrombin-activatable fibrinolysis inhibitor zymogen (TAFI). The enzyme TAFI is also referred to as plasma procarboxypeptidase B, procarboxypeptidase U or procarboxypeptidase R and is a proenzyme similar to carboxypeptidase B (L. Bajzar, Arterioscler. Thromb. Vasc. Biol. 2000, pages 2511-2518).

During formation of a clot, thrombin is generated as the final product of the coagulation cascade and induces conversion of soluble plasma fibrinogen to an insoluble fibrin matrix. At the same time, thrombin activates the endogenous fibrinolysis inhibitor TAFI. Activated TAFI (TAFIa) is thus produced during thrombus formation and lysis from the zymogen TAFI through the action of thrombin; thrombomodulin in a complex with thrombin increases this effect about 1250-fold. TAFIa cleaves basic amino acids at the carboxy end of fibrin fragments. The loss of carboxy-terminal lysines as binding sites for plasminogen then leads to inhibition of fibrinolysis. Efficient inhibitors of TAFIa prevent the loss of these high-affinity lysine binding sites for plasminogen and, in this way, assist endogenous fibrinolysis by plasmin: TAFIa inhibitors have profibrinolytic effects.

In order to maintain hemostasis in the blood, mechanisms which lead to the clotting of blood and to the breaking up of clots have developed; these are in equilibrium. If a disturbed equilibrium favors coagulation, fibrin is produced in larger quantities, so that pathological processes of thrombus formation may lead to serious pathological states in humans.

Just like excessive coagulation may lead to serious pathological states caused by thrombosis, an antithrombotic treatment entails the risk of unwanted bleeding through disturbance of the formation of a necessary hemostatic plug. Inhibition of TAFIa increases endogenous fibrinolysis—without influencing coagulation and platelet aggregation—i.e. the disturbed equilibrium is shifted in favor of fibrinolysis. It is thus possible both to counter the buildup of a clinically relevant thrombus, and to increase the lysis of a pre-existing clot. On the other hand, buildup of a hemostatic plug is not impaired, so that a hemorrhagic diathesis is probably not to be expected (Bouma et al., J. Thrombosis and Haemostasis, 1, 2003, pages 1566-1574).

Inhibitors of TAFIa have already been described in the International Applications WO03/013526 and WO2005/105781. A region-specific synthesis of N-substituted imidazoles from α-amino acids is described by Ning Xi et al; Tetrahedron Letters, Vol. 46, No. 43, 2005, pages 7315-7319.

The synthetic routes used to prepare compounds of formula in the prior art have synthetic strategies with a late introduction of the R1 group. This is shown in Scheme 1 and is highly advantageous for the elucidation of structure-activity-relationships as this strategy allows high diversity at the end of the synthesis. The synthetic routes described are long (7-8 steps) and start from expensive imidazoyl acetic acid 1 towards compound 6 or 7. This strategy necessitates the use of protection and deprotection sequences, thus severely limiting the synthetic efficiency.

Scheme 1

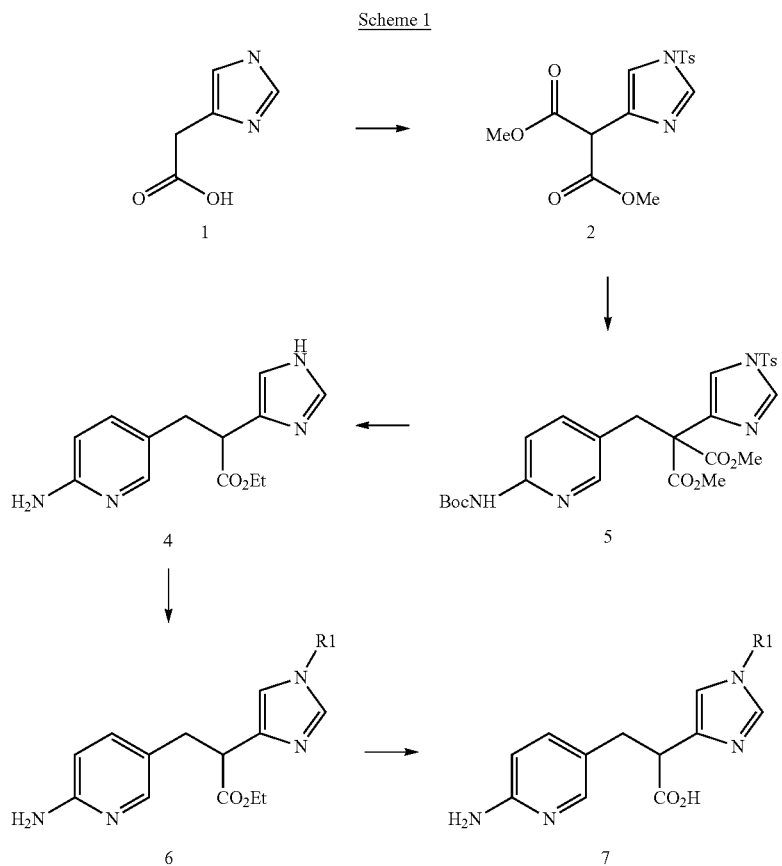

BRIEF SUMMARY OF THE INVENTION

It has now been found that the disadvantages mentioned can be avoided by a short and efficient synthetic route which also dispenses with costly and inconvenient purification steps such as column chromatography.

The object is achieved by using N1-substituted imidazoyl acetic acid derivatives as starting compounds for the synthetic route, which allows the preparation of a compound of formula I in a few chemical reaction steps, in good yields and with high purity.

The invention therefore relates to a process for obtaining the compound of the formula I

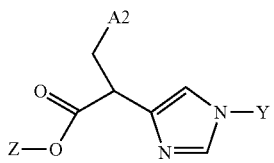

(I)

and/or all stereoisomeric forms of the compound of the formula I and/or mixtures of these forms in any ratio, where A2 is aminopyridyl, in which aminopyridyl is unsubstituted or substituted independently of one another once, twice or three times by halogen or methyl, Y is —($C_3$-$C_8$)-cycloalkyl, in which cycloalkyl is unsubstituted or substituted independently of one another once, twice or three times by R1, or the radical of the formula III

-A3-A5 (III)

wherein A3 is —($CH_2$)$_r$-Het in which Het is pyrrolidine, benzothiophene or piperidine, which is unsubstituted or substituted independently of one another once, twice or three times by R1, A5 is a)1) —C(O)—R3,
 a)2) —C(O)—N(R4)-R5,
 a)3) —($SO_2$)—R6 or
 a)4) —C(O)—O—R7,
 is the integer zero, 1, 2 or 3, where R1 is
 a) phenyl, where phenyl is unsubstituted or substituted once, twice or three times independently of one another by —($C_1$-$C_4$) alkyl,
 b) halogen,
 c) —($C_1$-$C_4$)-alkyl,
 d) —($C_3$-$C_6$)-cycloalkyl,
 e) —$CF_3$,
 f) —O—$CF_3$,
 g) triazolyl or
 h) pyridinyl, where R3, R6 and R7 are identical or different are independently of one another
 a) hydrogen atom,
 b) —($C_1$-$C_6$)-alkyl in which alkyl is unsubstituted or substituted independently of one another once, twice or three times by R1,
 c) phenyl in which phenyl is unsubstituted or substituted independently of one another once, twice or three times by R1, or
 d) —($C_3$-$C_6$)-cycloalkyl in which cycloalkyl is unsubstituted or substituted independently of one another once, twice or three times by R1, where R4 and R5 are identical or different are independently of one another
 a) hydrogen atom,
 b) —($C_1$-$C_6$)-alkyl or —($C_2$-$C_6$)-alkenyl, in which alkyl or alkenyl is unsubstituted or substituted independently of one another once, twice or three times by R1,
 c) phenyl in which phenyl is unsubstituted or substituted independently of one another once, twice or three times by R1, or
 d) —($C_3$-$C_6$)-cycloalkyl in which cycloalkyl is unsubstituted or substituted independently of one another once, twice or three times by R1, and Z is 1) —($C_1$-$C_6$)-alkyl,
 2) —($C_1$-$C_6$)-alkyl-OH,
 3) —($C_1$-$C_4$)-alkylene-($C_3$-$C_6$)-cycloalkyl,
 4) —$CH_2$-phenyl, wherein phenyl is unsubstituted or substituted once or twice by $NO_2$ or methoxy,
 5) —$CH_2$—CH=$CH_2$ or
 6) —($C_1$-$C_{10}$)-alkylene-O—C(O)—O—($C_3$-$C_6$)-cycloalkyl, which comprises A) reacting a compound of the formula IV

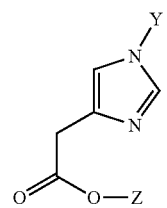

(IV)

with an oxalic acid diester of formula V

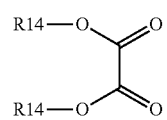

(V)

wherein R14 is —($C_1$-$C_6$)-alkyl, to give a compound of formula VI

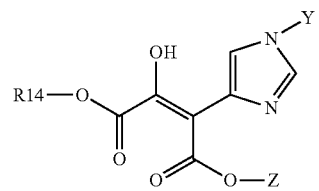

(VI)

B) reacting the compound of formula VI with the compound of formula VII

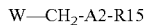

W—$CH_2$-A2-R15 (VII)

wherein W is a halogen or a sulfonyl ester, and R15 is an amino-protecting group, to give a compound of formula VIII

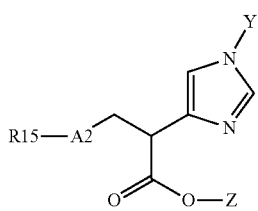

(VIII)

C) and reacting the compound of formula VIII to give a compound of formula I, or D) optionally a compound of the formula I which has been prepared by process steps A), B) and C) and occurs owing to its chemical structure in enantiomeric forms being fractionated by salt formation with enantiopure acids or bases, chromatography on chiral stationary phases or derivatization using chiral enantiopure compounds such as amino acids, separation of the diastereomers obtained in this way, and elimination of the chiral auxiliary groups into the pure enantiomers.

2) The invention also relates to a process for obtaining the compound of the formula I where A2 is aminopyridyl, in which aminopyridyl is unsubstituted or substituted independently of one another once, twice or three times by halogen or methyl, Y is —$(C_3$-$C_8)$-cycloalkyl, in which cycloalkyl is unsubstituted or substituted independently of one another once, twice or three times by R1, or the radical of the formula III

-A3-A5  (III)

wherein A3 is —$(CH_2)_r$-Het in which Het is pyrrolidine, benzothiophene or piperidine, which is unsubstituted or substituted independently of one another once, twice or three times by R1, A5 is a)1) —C(O)—R3,
 a)2) —C(O)—N(R4)-R5,
 a)3) —$(SO_2)$—R6 or
 a)4) —C(O)—O—R7,
 r is the integer zero, 1, 2 or 3, where R1 is
 a) phenyl, where phenyl is unsubstituted or substituted once, twice or three times independently of one another by —$(C_1$-$C_4)$ alkyl,
 b) halogen,
 c) —$(C_1$-$C_4)$-alkyl,
 d) —$(C_3$-$C_6)$-cycloalkyl,
 e) —$CF_3$,
 f) —O—$CF_3$,
 g) triazolyl or
 h) pyridinyl, where R3. R6 and R7 are identical or different are independently of one another
 a) hydrogen atom,
 b) —$(C_1$-$C_6)$-alkyl in which alkyl is unsubstituted or substituted independently of one another once, twice or three times by R1,
 c) phenyl in which phenyl is unsubstituted or substituted independently of one another once, twice or three times by R1, or
 d) —$(C_3$-$C_6)$-cycloalkyl in which cycloalkyl is unsubstituted or substituted independently of one another once, twice or three times by R1, where R4 and R5 are identical or different are independently of one another
 a) hydrogen atom,
 b) —$(C_1$-$C_6)$-alkyl or —$(C_2$-$C_6)$-alkenyl, in which alkyl or alkenyl is unsubstituted or substituted independently of one another once, twice or three times by R1,
 c) phenyl in which phenyl is unsubstituted or substituted independently of one another once, twice or three times by R1, or
 d) —$(C_3$-$C_6)$-cycloalkyl in which cycloalkyl is unsubstituted or substituted independently of one another once, twice or three times by R1, and Z is 1) —$(C_1$-$C_6)$-alkyl,
 2) —$(C_1$-$C_6)$-alkyl-OH,
 3) —$(C_0$-$C_4)$-alkylene-$(C_3$-$C_6)$-cycloalkyl or
 4) —$(C_1$-$C_{10})$-alkylene-O—C(O)—O—$(C_3$-$C_6)$-cycloalkyl.

3) The invention also relates to a process for obtaining the compound of the formula I where A2 is 2-aminopyridyl, which is unsubstituted or substituted independently of one another once, twice or three times by F, Cl, Br, I or methyl.

Y is —$(C_3$-$C_8)$-cycloalkyl, in which cycloalkyl is unsubstituted or substituted independently of one another once, twice or three times by R1, or the radical of the formula III, wherein A3 is —$(CH_2)_r$-Het in which Het is pyrrolidine or piperidine, which is unsubstituted or substituted independently of one another once, twice or three times by R1.

A5 is a)1) —C(O)—R3,
 a)2) —C(O)—N(R4)-R5,
 a)3) —$(SO_2)$—R6 or
 a)4) —C(O)—O—R7,
 r is the integer zero, 1, 2 or 3,
 where A5 is bonded to the nitrogen atom of A3, where R1 is
 a) phenyl, where phenyl is unsubstituted or substituted once, twice or three times independently of one another by —$(C_1$-$C_4)$ alkyl,
 b) fluorine,
 c) —$(C_1$-$C_4)$-alkyl,
 d) —$(C_3$-$C_6)$-cycloalkyl,
 e) —$CF_3$,
 f) —O—$CF_3$,
 g) chlorine,
 h) triazolyl or
 i) pyridinyl, where R3, R6 and R7 are identical or different are independently of one another
 a) —$(C_1$-$C_6)$-alkyl in which alkyl is unsubstituted or substituted independently of one another once, twice or three times by R1,
 b) phenyl in which phenyl is unsubstituted or substituted independently of one another once, twice or three times by R1, or
 c) —$(C_3$-$C_6)$-cycloalkyl in which cycloalkyl is unsubstituted or substituted independently of one another once, twice or three times by R1, where R4 and R5 are identical or different are independently of one another
 a) hydrogen atom,
 b) —$(C_1$-$C_6)$-alkyl or —$(C_2$-$C_6)$-alkenyl, in which alkyl or alkenyl is unsubstituted or substituted independently of one another once, twice or three times by R1,
 c) phenyl in which phenyl is unsubstituted or substituted independently of one another once, twice or three times by R1, or d) —($C_3$-$C_6$)-cycloalkyl in which cycloalkyl is unsubstituted or substituted independently of one another once, twice or three times by R1, and Z is —($C_1$-$C_6$)-alkyl or benzyl.

4) The invention further relates to a process for obtaining the compound of the formula I where A2 is 2-aminopyridyl.

Y is —($C_3$-$C_8$)-cycloalkyl, which is unsubstituted or substituted by one or two methyl or —$(CH_2)_r$-Het in which Het is pyrrolidine or piperidine, and Het is substituted by —C(O)—$(CH_2)_m$-Phenyl or —C(O)—CH-(Phenyl)$_2$ and m is the integer zero, 1 or 2, and Z is —($C_1$-$C_4$)-alkyl.

5) The invention further relates to a process for obtaining the compound of the formula I where A2 is 2-aminopyridyl.

Y is —($C_3$-$C_8$)-cycloalkyl, which is unsubstituted or substituted by one or two methyl and Z is —($C_1$-$C_4$)-alkyl.

DETAILED DESCRIPTION OF THE INVENTION

The term "($C_1$-$C_6$)-alkyl" or "($C_1$-$C_{10}$)-alkyl" means hydrocarbon radicals whose carbon chain is straight-chain or branched and comprises 1 to 6 carbon atoms or 1 to 10 carbon atoms, for example methyl, ethyl, propyl, isopropyl, butyl, isobutyl, tertiary butyl, pentyl, isopentyl, neopentyl, hexyl, 2,3-dimethylbutane, neohexyl, heptyl, octanyl, nonanyl or decanyl.

The term "—($C_0$-$C_4$)-alkylene" means hydrocarbon radicals whose carbon chain is straight-chain or branched and comprises 1 to 4 carbon atoms, for example methylene, ethylene, propylene, isopropylene, isobutylene, butylene or tertiary butylene. The term "—$C_0$-alkylene" is a covalent bond.

The term "—($C_2$-$C_{10}$)-alkenylene" means hydrocarbon radicals whose carbon chain is straight-chain or branched and comprises 2 to 10 carbon atoms and have, depending on the chain length, 1, 2 or 3 double bonds, for example ethenylene, propenylene, isopropenylene, isobutenylene or butenylene; the substituents on the double bond may, if the possibility exists in principle, be arranged in the E or Z configuration.

The term "($C_3$-$C_8$)-cycloalkyl" means radicals such as compounds derived from 3- to 8-membered monocycles such as cyclopropyl, cyclobutyl, cyclopentyl, cyclohexyl, cycloheptyl or cyclooctanyl.

The term "—$(CH_2)_r$—" in which r is the integer zero 1, 2 or 3" means radicals such as methylene, ethylene or propylene. In the case where r is the integer zero, the radical has the meaning of a covalent bond. The term "—$(CH_2)_m$— in which m is the integer zero 1 or 2" means radicals such as methylene or ethylene. In the case where m is the integer zero, the radical has the meaning of a covalent bond.

It should be noted in the partial formula III that the linkage to the 1H-imidazole takes place via A3 and not via A5.

The term "($C_1$-$C_6$)-alkyl-OH" means alcohols such as methanol, ethanol, 1-propanol, isopropanol, 1-butanol, isobutanol, sec-butanol, pentanol or hexanol.

The term "—$CH_2$-phenyl" means benzyl. The term "—$CH_2$—CH=$CH_2$" means allyl. The term "halogen" means fluorine, chlorine, bromine or iodine.

6) A further aspect of the invention relates to compounds of the formula VI

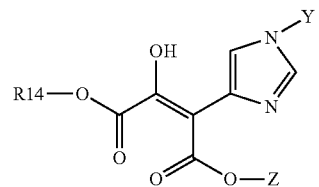

(VI)

wherein R14 is —($C_1$-$C_8$)-alkyl,

Y is —($C_3$-$C_8$)-cycloalkyl, in which cycloalkyl is unsubstituted or substituted independently of one another once, twice or three times by R1, or the radical of the formula III

-A3-A5 (III)

wherein A3 is —$(CH_2)_r$-Het in which Het is pyrrolidine, benzothiophene or piperidine, which is unsubstituted or substituted independently of one another once, twice or three times by R1, A5 is a)1) —C(O)—R3,
 a)2) —C(O)—N(R4)-R5,
 a)3) —(SO$_2$)—R6 or
 a)4) —C(O)—O—R7,
 r is the integer zero, 1, 2 or 3, wherein R1 is
 a) phenyl, where phenyl is unsubstituted or substituted once, twice or three times independently of one another by —($C_1$-$C_4$) alkyl,
 b) halogen,
 c) —($C_1$-$C_4$)-alkyl,
 d) —($C_3$-$C_8$)-cycloalkyl,
 e) —$CF_3$,
 f) —O—$CF_3$,
 g) triazolyl or
 h) pyridinyl, where R3, R6 and R7 are identical or different are independently of one another
 a) hydrogen atom,
 b) —($C_1$-$C_6$)-alkyl in which alkyl is unsubstituted or substituted independently of one another once, twice or three times by R1,
 c) phenyl in which phenyl is unsubstituted or substituted independently of one another once, twice or three times by R1, or
 d) —($C_3$-$C_6$)-cycloalkyl in which cycloalkyl is unsubstituted or substituted independently of one another once, twice or three times by R1, where R4 and R5 are identical or different are independently of one another
 a) hydrogen atom,
 b) —($C_1$-$C_6$)-alkyl or —($C_2$-$C_6$)-alkenyl, in which alkyl or alkenyl is unsubstituted or substituted independently of one another once, twice or three times by R1,
 c) phenyl in which phenyl is unsubstituted or substituted independently of one another once, twice or three times by R1, or
 d) —($C_3$-$C_6$)-cycloalkyl in which cycloalkyl is unsubstituted or substituted independently of one another once, twice or three times by R1, R14 is —($C_1$-$C_6$)-alkyl, and Z is 1) —($C_1$-$C_6$)-alkyl,
 2) —($C_1$-$C_6$)-alkyl-OH,
 3) —($C_1$-$C_4$)-alkylene-($C_3$-$C_6$)-cycloalkyl,
 4) —$CH_2$-phenyl, wherein phenyl is unsubstituted or substituted once or twice by $NO_2$ or methoxy,
 5) —$CH_2$—CH=$CH_2$ or 6) —($C_1$-$C_{10}$)-alkylene-O—C(O)—O—($C_3$-$C_6$)-cycloalkyl.
7) The invention further relates to compounds of the formula VI in which
R14 is —($C_1$-$C_6$)-alkyl,
Y is —($C_3$-$C_8$)-cycloalkyl, in which cycloalkyl is unsubstituted or substituted independently of one another once, twice or three times by R1, or the radical of the formula III

-A3-A5 (III)

wherein A3 is —($CH_2$)$_r$-Het in which Het is pyrrolidine, benzothiophene or piperidine, which is unsubstituted or substituted independently of one another once, twice or three times by R1,
A5 is a)1) —C(O)—R3,
 a)2) —C(O)—N(R4)-R5,
 a)3) —($SO_2$)—R6 or
 a)4) —C(O)—O—R7,
 r is the integer zero, 1, 2 or 3,
wherein R1 is
 a) phenyl, where phenyl is unsubstituted or substituted once, twice or three times independently of one another by —($C_1$-$C_4$) alkyl,
 b) halogen,
 c) —($C_1$-$C_4$)-alkyl,
 d) —($C_3$-$C_6$)-cycloalkyl,
 e) —$CF_3$,
 f) —O—$CF_3$,
 g) triazolyl or
 h) pyridinyl,
where R3, R6 and R7 are identical or different are independently of one another
 a) hydrogen atom,
 b) —($C_1$-$C_6$)-alkyl in which alkyl is unsubstituted or substituted independently of one another once, twice or three times by R1,
 c) phenyl in which phenyl is unsubstituted or substituted independently of one another once, twice or three times by R1, or
 d) —($C_3$-$C_6$)-cycloalkyl in which cycloalkyl is unsubstituted or substituted independently of one another once, twice or three times by R1,
where R4 and R5 are identical or different are independently of one another
 a) hydrogen atom,
 b) —($C_1$-$C_6$)-alkyl or —($C_2$-$C_6$)-alkenyl, in which alkyl or alkenyl is unsubstituted or substituted independently of one another once, twice or three times by R1,
 c) phenyl in which phenyl is unsubstituted or substituted independently of one another once, twice or three times by R1, or
 d) —($C_3$-$C_6$)-cycloalkyl in which cycloalkyl is unsubstituted or substituted independently of one another once, twice or three times by R1,
R14 is —($C_1$-$C_6$)-alkyl, and
Z is 1) —($C_1$-$C_6$)-alkyl,
2) —($C_1$-$C_6$)-alkyl-OH,
3) —($C_0$-$C_4$)-alkylene-($C_3$-$C_6$)-cycloalkyl or
4) —($C_1$-$C_{10}$)-alkylene-O—C(O)—O—($C_3$-$C_6$)-cycloalkyl.
8) The invention further relates to compounds of the formula VI in which R14 is —($C_1$-$C_6$)-alkyl,
Y is —($C_3$-$C_8$)-cycloalkyl, which is unsubstituted or substituted by one or two methyl or —($CH_2$)$_r$-Het in which Het is pyrrolidine or piperidine, and Het is substituted by —C(O)—($CH_2$)$_m$-Phenyl or —C(O)—CH-(Phenyl)$_2$ and m is the integer zero, 1 or 2,
and Z is —($C_1$-$C_4$)-alkyl or benzyl.

9) The invention further relates to compounds of the formula VI in which R14 is —($C_1$-$C_6$)-alkyl,
Y is —($C_3$-$C_8$)-cycloalkyl, which is unsubstituted or substituted by one or two methyl
and Z is —($C_1$-$C_4$)-alkyl.
10) The invention further relates to a process for obtaining compounds of the formula VI, which comprises reacting a compound of the formula IV

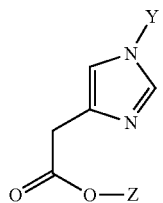

(IV)

wherein Y is —($C_3$-$C_8$)-cycloalkyl, in which cycloalkyl is unsubstituted or substituted independently of one another once, twice or three times by R1, or the radical of the formula III

-A3-A5 (III)

A3 is —($CH_2$)$_r$-Het in which Het is pyrrolidine, benzothiophene or piperidine, which is unsubstituted or substituted independently of one another once, twice or three times by R1,
A5 is a)1) —C(O)—R3,
 a)2) —C(O)—N(R4)-R5,
 a)3) —($SO_2$)—R6 or
 a)4) —C(O)—O—R7,
 r is the integer zero, 1, 2 or 3,
where R1 is
 a) phenyl, where phenyl is unsubstituted or substituted once, twice or three times independently of one another by —($C_1$-$C_4$) alkyl,
 b) halogen,
 c) —($C_1$-$C_4$)-alkyl,
 d) —($C_3$-$C_6$)-cycloalkyl,
 e) —$CF_3$,
 f) —O—$CF_3$,
 g) triazolyl or
 h) pyridinyl,
where R3, R6 and R7 are identical or different are independently of one another
 a) hydrogen atom,
 b) —($C_1$-$C_6$)-alkyl in which alkyl is unsubstituted or substituted independently of one another once, twice or three times by R1,
 c) phenyl in which phenyl is unsubstituted or substituted independently of one another once, twice or three times by R1, or
 d) —($C_3$-$C_6$)-cycloalkyl in which cycloalkyl is unsubstituted or substituted independently of one another once, twice or three times by R1,
where R4 and R5 are identical or different are independently of one another
 a) hydrogen atom,
 b) —($C_1$-$C_6$)-alkyl or —($C_2$-$C_6$)-alkenyl, in which alkyl or alkenyl is unsubstituted or substituted independently of one another once, twice or three times by R1,
 phenyl in which phenyl is unsubstituted or substituted independently of one another once, twice or three times by R1, or d) —$(C_3$-$C_6)$-cycloalkyl in which cycloalkyl is unsubstituted or substituted independently of one another once, twice or three times by R1, and Z is 1) —$(C_1$-$C_6)$-alkyl,
2) —$(C_1$-$C_6)$-alkyl-OH,
3) —$(C_1$-$C_4)$-alkylene-$(C_3$-$C_6)$-cycloalkyl,
4) —$CH_2$-phenyl, wherein phenyl is unsubstituted or substituted once or twice by $NO_2$ or methoxy,
5) —$CH_2$—CH=$CH_2$ or
6) —$(C_1$-$C_{10})$-alkylene-O—C(O)—O—$(C_3$-$C_6)$-cycloalkyl, with an oxalic diester of formula V

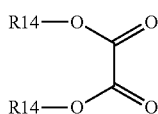

(V)

wherein R14 is —$(C_1$-$C_6)$-alkyl,
to give a compound of formula VI.

The compound of formula VI can occur in two tautomeric forms which are as follows:

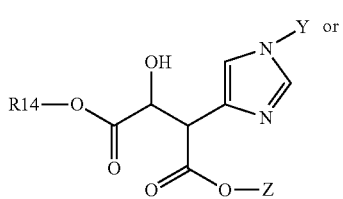

(VI)

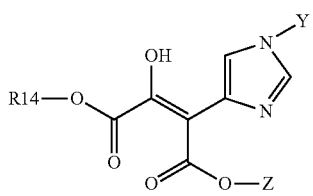

(VI)

11) A further aspect of the invention relates to compounds of the formula VIII

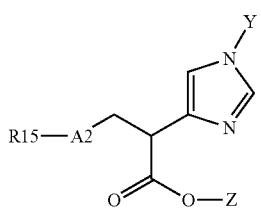

(VIII)

wherein,
R15 is an amino protecting group selected from tert-butyloxycarbonyl, benzyloxycarbonyl, p-methoxybenzylcarbonyl, N-formyl, N-acetyl, N-benzyl, N-1-(diphenyl)methyl, N-trityl, (4-methoxyphenyl)diphenylmethyl, N-dialkyl phosphoramidates and N-p-toluenesulfonyl.

A2 is aminopyridyl, in which aminopyridyl is unsubstituted or substituted independently of one another once, twice or three times by halogen or methyl, Y is —$(C_3$-$C_8)$-cycloalkyl, in which cycloalkyl is unsubstituted or substituted independently of one another once, twice or three times by R1, or the radical of the formula III

-A3-A5   (III)

wherein A3 is —$(CH_2)_r$-Het in which Het is pyrrolidine, benzothiophene or piperidine, which is unsubstituted or substituted independently of one another once, twice or three times by R1, A5 is a)1) —C(O)—R3,
a)2) —C(O)—N(R4)-R5,
a)3) —$(SO_2)$—R6 or
a)4) —C(O)—O—R7,
r is the integer zero, 1, 2 or 3, wherein R1 is
a) phenyl, where phenyl is unsubstituted or substituted once, twice or three times independently of one another by —$(C_1$-$C_4)$ alkyl,
b) halogen,
c) —$(C_1$-$C_4)$-alkyl,
d) —$(C_3$-$C_6)$-cycloalkyl,
e) —$CF_3$,
f) —O—$CF_3$,
g) triazolyl or
h) pyridinyl, where R3. R6 and R7 are identical or different are independently of one another
a) hydrogen atom,
b) —$(C_1$-$C_6)$-alkyl in which alkyl is unsubstituted or substituted independently of one another once, twice or three times by R1,
c) phenyl in which phenyl is unsubstituted or substituted independently of one another once, twice or three times by R1, or
d) —$(C_3$-$C_6)$-cycloalkyl in which cycloalkyl is unsubstituted or substituted independently of one another once, twice or three times by R1, where R4 and R5 are identical or different are independently of one another
a) hydrogen atom,
b) —$(C_1$-$C_6)$-alkyl or —$(C_2$-$C_6)$-alkenyl, in which alkyl or alkenyl is unsubstituted or substituted independently of one another once, twice or three times by R1,
c) phenyl in which phenyl is unsubstituted or substituted independently of one another once, twice or three times by R1, or
d) —$(C_3$-$C_6)$-cycloalkyl in which cycloalkyl is unsubstituted or substituted independently of one another once, twice or three times by R1, and Z is 1) —$(C_1$-$C_6)$-alkyl,
2) —$(C_1$-$C_6)$-alkyl-OH,
3) —$(C_1$-$C_4)$-alkylene-$(C_3$-$C_6)$-cycloalkyl,
4) —$CH_2$-phenyl, wherein phenyl is unsubstituted or substituted once or twice by $NO_2$ or methoxy,
5) —$CH_2$—CH=$CH_2$ or
6) —$(C_1$-$C_{10})$-alkylene-O—C(O)—O—$(C_3$-$C_6)$-cycloalkyl.

12) A further aspect of the invention relates to compounds of the formula VIII R15 is tert-butyloxycarbonyl,
A2 is 2-aminopyridyl,
Y is —$(C_3$-$C_8)$-cycloalkyl, which is unsubstituted or substituted by one or two methyl or —$(CH_2)_r$-Het in which Het is pyrrolidine or piperidine, and Het is substituted by —C(O)—$(CH_2)_m$-Phenyl or —C(O)—CH-$(Phenyl)_2$ and m is the integer zero, 1 or 2,
and Z is —$(C_1$-$C_4)$-alkyl or benzyl.

13) The invention further relates to a process for obtaining compounds of the formula VIII, which comprises reacting a compound of the formula VI with the compound of formula VII

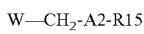   (VII)

wherein W is a halogen or a sulfonyl ester, and R15 is an amino-protecting group, to give a compound of formula VIII

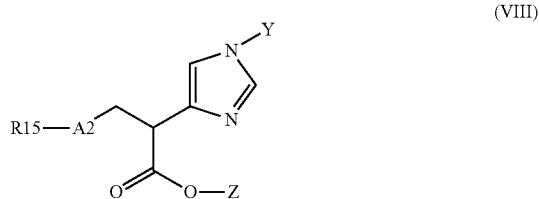   (VIII)

The reaction for process step A), which is the preparation of the compound of formula VI, may be carried out under the condition of a Claisen condensation (W. Wislicenus, *Chem. Ber.* 1886, 19, 3225). An imidazoyl acetic ester of formula IV is reacted with an oxalic diester of formula V under basic conditions to give a β-keto ester of formula VI (shown in enol form).

The imidazoyl acetic acid derivatives of formula IV can be prepared by the classical Marckwald synthesis (W. Marckwald, *Chem. Ber.* 1892, 25, 2354, N. Xi et al., *Tetrahedron Lett.* 2005, 46, 7315-7319) as shown in Scheme 2. The γ-amino β-ketoesters (formula II) can be synthesised according to literature (N. Xi et al., *Tetrahedron Lett.* 2005, 46, 7315-7319).

Scheme 2

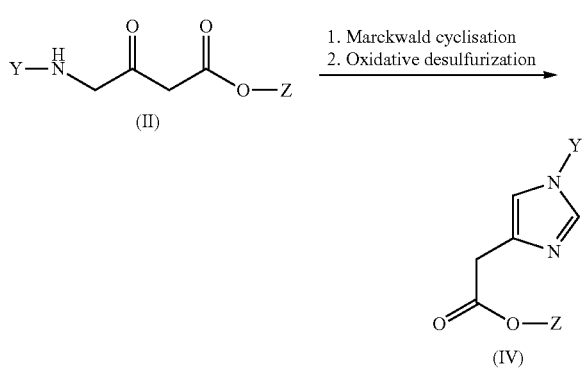

Oxalic diesters are well known in the art and commercially available from multiple vendors (e.g. Sigma-Aldrich Chemie GmbH, Eschenstraße 5, 82024 Taufkirchen, Germany). One of the oxalic diesters is oxalic acid diethyl ester.

In the preparation of the compound of the formula VI, a procedure is followed in such a manner that, first an imidazoyl acetic ester of formula IV is placed in a solvent and an oxalic diester of formula V and a base is added successively. The resultant solution or suspension is slowly cooled.

After an appropriate reaction time, the compound of the formula VI is precipitated out using a buffer or an acid. The compound of the formula VI is isolated, for example, by crystallization or extraction, for example using tetrahydrofuran or tert-butyl methyl ether. Crystallization is promoted by cooling the suspension or further evaporation of the solvents.

Solvents which can be used in reaction step A) are alcohols such as methanol, ethanol, propanol, isopropanol or butanol. Ethanol is preferred.

The base used in reaction step A) is an alkali metal alkoxide, e.g. sodium or potassium ethylate. Sodium ethylate is preferred. Alkali metal alkoxides are commercially available (Sigma-Aldrich). The alkali metal alkoxides can also be generated in situ from sodium or sodium hydride in alcohol or from a tertiary alkoxide such as potassium tert-butoxide or sodium or potassium amylate.

The temperature used is ranging from 0° C. to 100° C. depending on the boiling point of the solvent.

In the inventive reaction step A) from 100 mol to 200 mol (preferably 157 mol) of the compound of formula V and from 100 to 200 mol of base (preferably 133 mol) are used per 100 mol of the compound of formula IV. The amount of solvent used is generally from 5 l to 15 l (preferably 10 l) per kg of the compound of formula IV.

The reaction for process step B), which is the preparation of the compound of formula VIII, may be carried out under the condition of a retro Claisen condensation (W. Wislicenus, *Chem. Ber.* 1891, 24, 1257; J. M. Cook et al., *J. Am. Chem. Soc.* 1982, 104, 318). A β-keto ester of formula VI is reacted with an alkylating agent of formula VII under basic conditions to give a compound of formula VIII.

The alkylating agent of formula VII used in process step B) is known in the prior art and can be prepared as described in International Applications WO03/013526 and WO2005/105781.

R15 is an amino protecting group and can be selected from a variety of groups e.g. listed but not limited to those mentioned in T. W. Greene and P. G. M. Wuts: *Protective Groups in Organic Synthesis*, Third Edition, John Wiley and Sons, New York, 1999, 518-525, 531-540. The amino protecting group chosen is stable under the basic reaction conditions in process step B) and can be selected e.g. from carbamates, such as tert-butyloxycarbonyl and benzyloxycarbonyl or p-methoxybenzylcarbonyl, amides, such as N-formyl or N-acetyl, N-alkylaryls such as N-benzyl, N-1-(diphenyl)methyl, N-trityl or (4-methoxyphenyl)diphenylmethyl or N—P and N-sulfonyl protecting groups such as N-dialkyl phosphoramidates and N-p-toluenesulfonyl. A specified protecting group is tert-butyloxycarbonyl.

The residue W in alkylating agent of formula VII can be selected from halogens such as chloro, bromo, iodo or from sulfonyl esters such as mesylate, tosylate, nosylate, brosylate, triflate or nonaflate. A specified residua W is bromo and chloro.

In the preparation of the compound of the formula VIII, a procedure is followed in such a manner that, first a compound of formula VI is placed in a solvent and a base is added successively. The resultant solution or suspension is stirred for some time. Then a compound of formula VII is added successively. Optionally catalytic amounts of Tetra-(n)-butylammonium iodide (nBu4NI) can also be added successively.

After an appropriate reaction time water is added and the pH of the reaction mixture is adjusted to be above a pH of 9.0, preferably 10.5. The compound of the formula VIII is isolated, for example, by crystallization or extraction, for example using tetrahydrofuran or tert.-butyl methyl ether. Crystallization is promoted by cooling the suspension or further evaporation of the solvents.

Suitable bases for reaction step B) are all bases that are strong enough to form the enolate anion from the compound of formula VI. Examples for such bases are alkali metal amides, metal hydrides, alkoxides, amines bases or phosphazenes. The useful bases are e.g. alkali metal hexamethyldisilazide (MHMDS), another base is the lithium base (LiH-MDS), which can be obtained commercially (Sigma-Aldrich). Other bases are lithium diisopropylamide (LDA) or alkali alkoxides, such as lithium-, sodium- or potassium-tert-butoxide or lithium-, sodium- or potassium ethoxide, or amine bases, such as 1,5-diazabicyclo[4.3.0]non-5-ene (DBN); 1,8-diazabicyclo[5.4.0]undec-7-ene (DBU) or phosphazene bases such as 2-tert-butylimino-2-diethylamino-1,3-dimethyl-perhydro-1,3,2-diazaphosphorine (BEMP).

Solvents which can be used in reaction step B) are solvents compatible with the basic reaction conditions, such as ethers or alcohols. Ethers are exemplified by, but not limited to tetrahydrofuran (THF), methyl-tert.-butyl ether (MTBE), dioxane, dimethoxymethane (DME) or 2-methyl tetrahydrofuran. Tetrahydrofuran is preferred. Alcohols are exemplified by, but not limited to methyl alcohol (MeOH), ethyl alcohol (Ethanol), propyl alcohol (PrOH), iso-propyl alcohol (iPrOH), butyl alcohol (BuOH), ter.t-butyl alcohol (tBuOH). Ethanol is preferred.

The temperature used is ranging from −78° C. to 100° C. depending on the freezing point and the boiling point of the solvent.

In the inventive reaction step B) from 100 mol to 300 mol of the compound of formula VII and from 100 to 250 mol of base are used per 100 mol of the compound of formula VI. The amount of solvent used is generally from 5 l to 15 l per kg of the compound of formula VI.

The retro Claisen condensation leading to the monoalkylated product of formula VIII can be performed under aqueous basic conditions at pH>9.0, preferably 10.5. Useful bases are aqueous alkalimetal carbonate such as potassium carbonate or alkalimetal hydroxide such as sodium hydroxide. The base can be added when the preceding alkylation reaction had been finished or it can be generated from the base used for the alkylation step by the addition of water.

The crude compound of formula VIII so obtained can be isolated by standard aqueous work-up procedures and can be purified, by for e.g. chromatography. More useful is purification by crystallisation or digestion. Suitable solvents for this operation are again, among others, ethers such as tetrahydrofuran (THF) and more preferably tert-butyl methyl ether (MTBE).

The reaction for process step C), which is the preparation of the compound of formula I, by deprotection of the amino protecting group R15. Deprotection can be performed under standard conditions as described in T. W. Greene and P. G. M. Wuts: *Protective Groups in Organic Synthesis*, Third Edition, John Wiley and Sons, New York, 1999, 518-525, 531-540 and depends on the type of protecting group R15 utilized.

If R15 is tert-butoxycarbonyl, deprotection can be performed under acidic conditions. A possible method is acid in a protic solvent. Useful acids are mineral acids such as HBr, HCl, HI, $H_2SO_4$, $H_3PO_4$, Organic based acids such as acetic acid, trifluoromethane sulfonic acid or trifluoroacetic acid can also be used, preferred is acetic acid. Solvents used in this step are ether type solvents such as THF, dioxane or MTBE, or protic solvents such as water or alcohols. A specified ester Z is ethyl and water is a specified solvent, which can be used in process step C).

The temperature used is ranging from 0° C. to 100° C. depending on the boiling point of the solvent.

In the inventive reaction step C) from 1400 mol to 3000 mol of the acid are used per 100 mol of the compound of formula VIII. The amount of solvent used is generally from 5 l to 15 l per kg of the compound of formula VIII.

In process step D), the compound of the formula I is, if it occurs as mixture of diastereomers or enantiomers or results as mixtures thereof, separated into the pure stereoisomers either by chromatography on an optionally chiral support material or, if the racemic compound of the formula I is able to form salts, by fractional crystallization of the diastereomeric salts formed with an optically active base or acid as aid. Chiral stationary phases suitable for thin-layer or column chromatography to separate enantiomers are, for example, modified silica gel supports (so-called Pirkle phases) and high molecular weight carbohydrates such as triacetylcellulose. It is also possible to use for analytical purposes gas chromatographic methods on chiral stationary phases after appropriate derivatization known to the skilled worker. To separate enantiomers of the racemic carboxylic acids, diastereomeric salts differing in solubility are formed using an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is also possible to use enzymes, such as esterases, in the in the resolution of racemic mixtures to the pure enantiomers. It is further possible in the same way in principle to convert the racemic compounds of the formula I containing a basic group such as an amino group with optically active acids such as (+)-camphor-10-sulfonic acid, D- and L-tartaric acid, D- and L-lactic acid and (+) and (−)-mandelic acid into the pure enantiomers. Chiral compounds containing alcohol or amine functions can also be converted with appropriately activated or, where appropriate, N-protected enantiopure amino acids into the corresponding esters or amides, or conversely chiral carboxylic acids can be converted with carboxyl-protected enantiopure amino acids into the amides or with enantiopure hydroxy carboxylic acids such as lactic acid into the corresponding chiral esters. The chirality of the amino acid or alcohol residue introduced in enantiopure form can then be utilized for separating the isomers by carrying out a separation of the diastereomers which are now present by crystallization or chromatography on suitable stationary phases and than eliminating the included chiral moiety by suitable methods.

A further possibility with some of the compounds of the invention is to employ diastereomerically or enantiomerically pure starting materials to prepare the framework structures. It is thus possible where appropriate also to employ other or simplified processes for purifying the final products.

It is possible that the sequence of the reactions steps might vary.

14) A further aspect of the invention relates to compounds of the formula IV

(IV)

wherein
Y is —($C_3$-$C_8$)-cycloalkyl, in which cycloalkyl is unsubstituted or substituted independently of one another once, twice or three times by R1, or the radical of the formula III

-A3-A5  (III)

A3 is —(CH₂)$_r$-Het in which Het is pyrrolidine, benzothiophene or piperidine, which is unsubstituted or substituted independently of one another once, twice or three times by R1,
A5 is a)1) —C(O)—R3,
   a)2) —C(O)—N(R4)-R5,
   a)3) —(SO₂)—R6 or
   a)4) —C(O)—O—R7,
   r is the integer zero, 1, 2 or 3,
where R1 is
   a) phenyl, where phenyl is unsubstituted or substituted once, twice or three times independently of one another by —(C₁-C₄) alkyl,
   b) halogen,
   c) —(C₁-C₄)-alkyl,
   d) —(C₃-C₆)-cycloalkyl,
   e) —CF₃,
   f) —O—CF₃,
   g) triazolyl or
   h) pyridinyl,
where R3, R6 and R7 are identical or different are independently of one another
   a) hydrogen atom,
   b) —(C₁-C₆)-alkyl in which alkyl is unsubstituted or substituted independently of one another once, twice or three times by R1,
   c) phenyl in which phenyl is unsubstituted or substituted independently of one another once, twice or three times by R1, or
   d) —(C₃-C₆)-cycloalkyl in which cycloalkyl is unsubstituted or substituted independently of one another once, twice or three times by R1,
where R4 and R5 are identical or different are independently of one another
   a) hydrogen atom,
   b) —(C₁-C₆)-alkyl or —(C₂-C₆)-alkenyl, in which alkyl or alkenyl is unsubstituted or substituted independently of one another once, twice or three times by R1,
   c) phenyl in which phenyl is unsubstituted or substituted independently of one another once, twice or three times by R1, or
   d) —(C₃-C₆)-cycloalkyl in which cycloalkyl is unsubstituted or substituted independently of one another once, twice or three times by R1, and
Z is 1) —(C₁-C₆)-alkyl,
   2) —(C₁-C₆)-alkyl-OH,
   3) —(C₁-C₄)-alkylene-(C₃-C₆)-cycloalkyl,
   4) —CH₂-phenyl, wherein phenyl is unsubstituted or substituted once or twice by NO₂ or methoxy,
   5) —CH₂—CH=CH₂ or
   6) —(C₁-C₁₀)-alkylene-O—C(O)—O—(C₃-C₆)-cycloalkyl.
15) The invention further relates to compounds of the formula IV in which
Y is —(C₃-C₈)-cycloalkyl, which is unsubstituted or substituted by one or two methyl or —(CH₂)$_r$-Het in which Het is pyrrolidine or piperidine, and Het is substituted by —C(O)—(CH₂)$_m$-Phenyl or —C(O)—CH-(Phenyl)₂ and m is the integer zero, 1 or 2,
and Z is —(C₁-C₄)-alkyl.
16) The invention further relates to compounds of the formula IV in which
Y is —(C₃-C₈)-cycloalkyl, which is unsubstituted or substituted by one or two methyl
and Z is —(C₁-C₄)-alkyl.

17) In a further embodiment a process according to the present invention is applicable for the preparation of the compounds of formula IV, (IV)

wherein
Y is —(C₃-C₈)-cycloalkyl, in which cycloalkyl is unsubstituted or substituted independently of one another once, twice or three times by R1, or the radical of the formula III

-A3-A5    (III)

A3 is —(CH₂)$_r$-Het in which Het is pyrrolidine, benzothiophene or piperidine, which is unsubstituted or substituted independently of one another once, twice or three times by R1,
A5 is a)1) —C(O)—R3,
   a)2) —C(O)—N(R4)-R5,
   a)3) —(SO₂)—R6 or
   a)4) —C(O)—O—R7,
   r is the integer zero, 1, 2 or 3,
where R1 is
   a) phenyl, where phenyl is unsubstituted or substituted once, twice or three times independently of one another by —(C₁-C₄) alkyl,
   b) halogen,
   c) —(C₁-C₄)-alkyl,
   d) —(C₃-C₆)-cycloalkyl,
   e) —CF₃,
   f) —O—CF₃,
   g) triazolyl or
   h) pyridinyl,
where R3. R6 and R7 are identical or different are independently of one another
   a) hydrogen atom,
   b) —(C₁-C₆)-alkyl in which alkyl is unsubstituted or substituted independently of one another once, twice or three times by R1,
   c) phenyl in which phenyl is unsubstituted or substituted independently of one another once, twice or three times by R1, or
   d) —(C₃-C₆)-cycloalkyl in which cycloalkyl is unsubstituted or substituted independently of one another once, twice or three times by R1,
where R4 and R5 are identical or different are independently of one another
   a) hydrogen atom,
   b) —(C₁-C₆)-alkyl or —(C₂-C₆)-alkenyl, in which alkyl or alkenyl is unsubstituted or substituted independently of one another once, twice or three times by R1,
   c) phenyl in which phenyl is unsubstituted or substituted independently of one another once, twice or three times by R1, or
   d) —(C₃-C₆)-cycloalkyl in which cycloalkyl is unsubstituted or substituted independently of one another once, twice or three times by R1, and
Z is 1) —(C₁-C₆)-alkyl,
   2) —(C₁-C₆)-alkyl-OH,
   3) —(C₁-C₄)-alkylene-(C₃-C₆)-cycloalkyl,
   4) —CH₂-phenyl, wherein phenyl is unsubstituted or substituted once or twice by NO₂ or methoxy, 5) —CH₂—CH═CH₂ or
6) —(C₁-C₁₀)-alkylene-O—C(O)—O—(C₃-C₆)-cycloalkyl,
which comprises
a) reacting a compound of the formula II

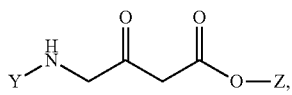

with a thiocyanate salt to give a compound of formula IX,

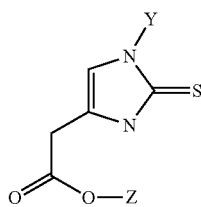

and
b) the compound of formula IX is desulfurizated to give a compound of formula IV.
18) A further aspect of the invention relates to compounds of the formula IX

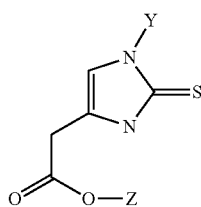

wherein Y is —(C₃-C₈)-cycloalkyl, in which cycloalkyl is unsubstituted or substituted independly of one another once, twice or three times by R1, or the radical of the formula III

-A3-A5    (III)

A3 is —(CH₂)ᵣ-Het in which Het is pyrrolidine, benzothiophene or piperidine, which is unsubstituted or substituted independently of one another once, twice or three times by R1,
A5 is a)1) —C(O)—R3,
  a)2) —C(O)—N(R4)-R5,
  a)3) —(SO₂)—R6 or
  a)4) —C(O)—O—R7,
  r is the integer zero, 1, 2 or 3,
where R1 is
  a) phenyl, where phenyl is unsubstituted or substituted once, twice or three times independently of one another by —(C₁-C₄) alkyl,
  b) halogen,
  c) —(C₁-C₄)-alkyl,
  d) —(C₃-C₆)-cycloalkyl,
  e) —CF₃,
  f) —O—CF₃,
  g) triazolyl or
  h) pyridinyl, where R3, R6 and R7 are identical or different are independently of one another
  a) hydrogen atom,
  b) —(C₁-C₆)-alkyl in which alkyl is unsubstituted or substituted independently of one another once, twice or three times by R1,
  c) phenyl in which phenyl is unsubstituted or substituted independently of one another once, twice or three times by R1, or
  d) —(C₃-C₆)-cycloalkyl in which cycloalkyl is unsubstituted or substituted independently of one another once, twice or three times by R1,
where R4 and R5 are identical or different are independently of one another
  a) hydrogen atom,
  b) —(C₁-C₆)-alkyl or —(C₂-C₆)-alkenyl, in which alkyl or alkenyl is unsubstituted or substituted independently of one another once, twice or three times by R1,
  c) phenyl in which phenyl is unsubstituted or substituted independently of one another once, twice or three times by R1, or
  d) —(C₃-C₆)-cycloalkyl in which cycloalkyl is unsubstituted or substituted independently of one another once, twice or three times by R1, and
Z is 1) —(C₁-C₆)-alkyl,
  2) —(C₁-C₆)-alkyl-OH,
  3) —(C₁-C₄)-alkylene-(C₃-C₆)-cycloalkyl,
  4) —CH₂-phenyl, wherein phenyl is unsubstituted or substituted once or twice by NO₂ or methoxy,
  5) —CH₂—CH═CH₂ or
  6) —(C₁-C₁₀)-alkylene-O—C(O)—O—(C₃-C₆)-cycloalkyl.
19) The invention further relates to compounds of the formula IX in which
Y is —(C₃-C₈)-cycloalkyl, which is unsubstituted or substituted by one or two methyl or —(CH₂)ᵣ-Het in which Het is pyrrolidine or piperidine, and Het is substituted by —C(O)—(CH₂)ₘ-Phenyl or —C(O)—CH-(Phenyl)₂ and m is the integer zero, 1 or 2,
and Z is —(C₁-C₄)-alkyl.
20) The invention further relates to compounds of the formula IX in which
Y is —(C₃-C₈)-cycloalkyl, which is unsubstituted or substituted by one or two methyl
and Z is —(C₁-C₄)-alkyl.
21) In a further embodiment a process according to the present invention is applicable for the preparation of the compounds of formula IX,

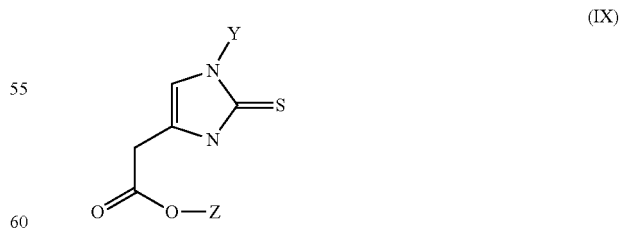

wherein
Y is —(C₃-C₈)-cycloalkyl, in which cycloalkyl is unsubstituted or substituted independently of one another once, twice or three times by R1, or the radical of the formula III

-A3-A5    (III)

A3 is —(CH$_2$)$_r$-Het in which Het is pyrrolidine, benzothiophene or piperidine, which is unsubstituted or substituted independently of one another once, twice or three times by R1, A5 is a)1) —C(O)—R3,
  a)2) —C(O)—N(R4)-R5,
  a)3) —(SO$_2$)—R6 or
  a)4) —C(O)—O—R7,
r is the integer zero, 1, 2 or 3,
where R1 is
  a) phenyl, where phenyl is unsubstituted or substituted once, twice or three times independently of one another by —(C$_1$-C$_4$) alkyl,
  b) halogen,
  c) —C$_4$)-alkyl,
  d) —(C$_3$-C$_6$)-cycloalkyl,
  e) —CF$_3$,
  f) —O—CF$_3$,
  g) triazolyl or
  h) pyridinyl,
where R3. R6 and R7 are identical or different are independently of one another
  a) hydrogen atom,
  b) —(C$_1$-C$_6$)-alkyl in which alkyl is unsubstituted or substituted independently of one another once, twice or three times by R1,
  c) phenyl in which phenyl is unsubstituted or substituted independently of one another once, twice or three times by R1, or
  d) —(C$_3$-C$_6$)-cycloalkyl in which cycloalkyl is unsubstituted or substituted independently of one another once, twice or three times by R1,
where R4 and R5 are identical or different are independently of one another
  a) hydrogen atom,
  b) —(C$_1$-C$_6$)-alkyl or —(C$_2$-C$_6$)-alkenyl, in which alkyl or alkenyl is unsubstituted or substituted independently of one another once, twice or three times by R1,
  c) phenyl in which phenyl is unsubstituted or substituted independently of one another once, twice or three times by R1, or
  d) —(C$_3$-C$_6$)-cycloalkyl in which cycloalkyl is unsubstituted or substituted independently of one another once, twice or three times by R1, and
Z is 1) —(C$_1$-C$_6$)-alkyl,
  2) —(C$_1$-C$_6$)-alkyl-OH,
  3) —(C$_1$-C$_4$)-alkylene-(C$_3$-C$_6$)-cycloalkyl,
  4) —CH$_2$-phenyl, wherein phenyl is unsubstituted or substituted once or twice by NO$_2$ or methoxy,
  5) —CH$_2$—CH=CH$_2$ or
  6) —(C$_1$-C$_{10}$)-alkylene-O—C(O)—O—(C$_3$-C$_6$)-cycloalkyl,
which comprises reacting a compound of the formula II

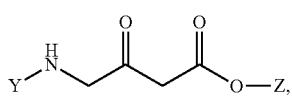

(II)

with a thiocyanate salt to give a compound of formula IX.

In the preparation of the compound of the formula IV, a procedure is followed in such a manner that, first an α-aminocarbonyl compound of formula II or a salt thereof is placed in a solvent mixture of water and an alcohol and a thiocyanate salt such as KSCN or NaSCN is added successively. The resultant solution or suspension is heated. After an appropriate reaction time the mixture is cooled to room temperature and the compound of formula IX is extracted or crystallized from the aqueous phase. Extraction can be performed by ethyl acetate. Crystallization is promoted by cooling the suspension or further evaporation of the solvents.

Solvents which can be used in said reaction are alcohols such as methanol, ethanol, propanol, isopropanol, tert.-butanol or butanol. tert.-Butanol is preferred.

The temperature used is ranging from 0° C. to 100° C. depending on the boiling point of the solvent.

In the inventive reaction step for the preparation of the compounds of formula IX from 100 mol to 300 mol of the thiocyanate salt are used per 100 mol of the compound of formula II. The amount of the used alcohol is generally from 0.2 l to 5 l per kg of the compound of formula II. The relation from water to alcohol is generally in the range from 5:1 to 1:3.

The compound of formula II can be prepared by methods known from the literature such as described in K. Satoh et al., *Chem. Pharm. Bull.* 1998, 46, 587.

Conversion of the cyclic thioureas of formula IX to the corresponding imidazoles can be achieved under oxidative conditions to remove the sulphur. First the compound of formula IX was dissolved in a suitable solvent and was slowly added to H$_2$O$_2$ in the same solvent. The resultant solution or suspension is cooled to a temperature in the range e.g. from 0° C. to 10° C. After addition the cooling was removed and the mixture was allowed stirring for 1 hour.

The received mixture was poured into solution of Na$_2$SO$_3$ in water and ice. The slurry was concentrated and the acidic residue was treated with saturated aqueous K$_2$CO$_3$ and saturated aqueous NaHCO$_3$ (pH 8). The mixture was extracted with Ethyl acetate.

Solvents which can be used in the oxidative desulphurization reaction are organic acids such as acetic acid, glacial acetic acid, optionally in combination with alcohols such as methanol or ethanol, esters such as methylacetate, ethylacetate, iso-propylacetate, tert-butylacetate, optionally in the presence of a base such as pyridine, 2-methylpyridine, 2,6-dimethylpyridine or alcohols such as methanol, ethanol, isopropanol, n-butanol, optionally in the presence of a catalytic amount of tungstene derivatives such as tungstic acid or sodium tungstate dihydrate.

The concentration of the solution of H$_2$O$_2$ can be in a range from 10% to 100%; in the solvent used; preferably about 30%.

In the inventive reaction step for the preparation of the compounds of formula IV from 300 mol to 500 mol of H$_2$O$_2$ are used per 100 mol of the compound of formula IX. The amount of acid is generally from 1 l to 8 l per kg of the compound of formula IX. The relation from acid to alcohol is generally in the range from 5:1 to 1:1.

Conversion of the cyclic thioureas of formula IX to the corresponding imidazoles appears also to be possible under reductive conditions to remove the sulphur.

The invention is illustrated in detail below with reference to examples.

End products are determined generally by $^1$H NMR (400 MHz, in CDCl$_3$ or DMSO-d$_6$). Temperature data are in degrees Celsius, RT means room temperature (22° C. to 26° C.), min means minute. t$_R$ means retention time. TFA means trifluoroacetic acid. MeCN means acetonitrile. Abbreviations used are either explained or correspond to the customary conventions.

Example 1

(E)-2-(1-Cyclohexyl-1H-imidazol-4-yl)-3-hydroxy-but-2-enedioic acid diethyl ester 54 g (0.23 mol) (1-Cyclohexyl-1H-imidazol-4-yl)-acetic acid ethyl ester were dissolved in 300 ml absolute Ethanol. Diethyl oxalate (77 ml, 0.57 mmol), followed by sodium ethylate (23 g, 0.34 mol) were added successively thereby the temperature rose to 35° C. The mixture was allowed to cool slowly down to 25° C. within one hour. The solution was concentrated and poured into 1 liter (l) phosphate buffer (pH=6.2, c=0.8 M). The yellow-brown solid was filtered and washed with 300 ml of water. The solid was then dried under reduced pressure at 60° C. The dry residue was digested with 300 ml of preferably tert.-butyl methyl ether (MTBE) at 40° C. for 2 hours, cooled to RT, filtered and dried on air to gave 53 g (0.16 mol, 69%) (E)-2-(1-Cyclohexyl-1H-imidazol-4-yl)-3-hydroxy-but-2-enedioic acid diethyl ester as an off white solid.

$^1$H-NMR (400 MHz, $d_6$-DMSO): δ=1.17 (t, J=7.1 Hz, 3H), 1.23 (t, J=7.2 Hz, 3H), 1.20-1.29 (m, 1H), 1.30-1.44 (m, 2H), 1.61-1.77 (m, 3H), 1.78-1.88 (m, 2H), 1.98-2.07 (m, 2H), 4.03 (q, J=7.1 Hz, 2H), 4.10 (q, J=7.1 Hz, 2H), 4.22-4.31 (m, 1H), 7.49 (d, J=1.8 Hz, 1H), 8.57 (d, J=1.7 Hz, 1H), 13.4-14.1 (bs, 1H);

HPLC: $t_R$=1.10 min (YMC J' sphere ODS H 80 20×2.1 mm, 4 μm, A: $H_2O$+0.05% TFA, B: MeCN, 4%→95% B in 2 min, 1 ml/min, 30° C.);

Mass (ES+) ($C_{17}H_{24}N_2O_5$): calculated. 366. found 337 [M+H]$^+$.

Melting point (Mp): >150° C. decomposition. (tert-butyl methyl ether; MTBE).

Example 2

3-(6-tert-Butoxycarbonylamino-pyridin-3-yl)-2-(1-cyclohexyl-1H-imidazol-4-yl)-propionic acid ethyl ester The compound prepared according to example 1 (5.0 g, 14.9 mmol) was suspended in 80 ml Tetrahydrofuran (THF) and Lithium hexamethyldisilazide (LiHMDS) (16.4 ml, 16.4 mmol, 1.0 M in THF) was added at RT. The mixture was stirred for 20 min, Tetra-(n)-butylammonium iodide (catalytic) was added, followed by (5-Bromomethyl-pyridin-2-yl)-carbamic acid tert-butyl ester (4.48 g, 15.6 mmol). After one hour water (20 ml), Ethyl acetate (AcOEt; 50 ml) were added and the pH-value was adjusted to 10.5 with saturated $K_2CO_3$. The mixture was allowed stirring for 90 min. The phases were separated and the aqueous layer was extracted with AcOEt (2×20 ml). The combined organic layers were washed with brine (20 ml), dried with $MgSO_4$ and concentrated to yield a red-orange crude product. The residue was treated with 50 ml MTBE and stirred for 30 min at 60° C. After cooling to RT the solid was filtered and washed with cold MTBE to yield the title compound (3.1 g, 7.0 mmol, 47%) as a yellowish solid.

$^1$H-NMR (500 MHz, $d_6$-DMSO): δ=1.05 (t, J=7.1 Hz, 3H), 1.13-1.24 (m, 1H), 1.29-1.40 (m, 2H), 1.46 (s, 9H), 1.53-1.67 (m, 3H), 1.74-1.82 (m, 2H), 1.88-1.96 (m, 2H), 3.76-3.81 (m, 1H), 3.91-4.05 (m, 3H), 7.05 (s, 1H), 7.48 (dd, J=8.6, 1.9 Hz, 1H), 7.58 (s, 1H), 7.64 (d, J=8.6 Hz, 1H), 7.99 (d, J=1.9 Hz, 1H), 9.62 (s, 1H);

HPLC: $t_R$=1.00 min (YMC J' sphere ODS H 80 20×2.1 mm, 4 μm, A: $H_2O$+0.05% TFA, B: MeCN, 4%→95% B in 2 min, 1 ml/min, 30° C.);

Mass (ES+) ($C_{24}H_{34}N_4O_4$): calculated. 442. found 443 [M+H]$^+$. Mp: 161-163° C. (MTBE).

Example 3

3-(6-Amino-pyridin-3-yl)-2-(1-cyclohexyl-1H-imidazol-4-yl)-propionic acid ethyl ester 39.0 g (88.1 mmol) 3-(6-tert-Butoxycarbonylamino-pyridin-3-yl)-2-(1-cyclohexyl-1H-imidazol-4-yl)-propionic acid ethyl ester as prepared in Example 2 were suspended in 200 ml Ethanol (EtOH) at RT. The mixture was saturated with HCl and was then refluxed for 2 h. The mixture was concentrated and the residue was treated with saturated aqueous $K_2CO_3$ (pH 9.0). The aqueous layer was extracted with AcOEt (3×200 ml). The combined organic layers were washed with brine (100 ml), dried with $MgSO_4$ and concentrated to yield the title compound (30 g, 87.6 mmol, 99%) as brown oil.

HPLC: $t_R$=0.69 min (YMC J' sphere ODS H 80 20×2.1 mm, 4 μm, A: $H_2O$+0.05% TFA, B: MeCN, 4%→95% B in 2 min, 1 ml/min, 30° C.);

Mass (ES+) ($C_{19}H_{26}N_4O_2$): calculated. 342. found 343 [M+H]$^+$.

Example 4

(1-Cyclohexyl-1H-imidazol-4-yl)-acetic acid ethyl ester 200 g (0.758 mol) 4-Cyclohexylamino-3-oxo-butyric acid ethyl ester hydrochloride were dissolved in 360 ml water and 120 ml tert-butanol and were heated to 90° C. Then 88.4 g (0.91 mol) KSCN were added and the mixture was heated for 20 s, thereby a phase separation occurred. After cooling to RT, the phases were separated and the aqueous layer was extracted with AcOEt. The combined organic layers were washed with Brine, dried with $MgSO_4$ and concentrated. The solid was digested in MTBE and filtered to yield 192 g (0.715 mol, 94%) of (1-Cyclohexyl-2-thioxo-2,3-dihydro-1H-imidazol-4-yl)-acetic acid ethyl ester as a beige solid. HPLC: $t_R$=1.16 min (YMC J' sphere ODS H 80 20×2.1 mm, 4 μm, A: $H_2O$+0.05% TFA, B: MeCN, 4%→95% B in 2 min, 1 ml/min, 30° C.); Mass (ES+) ($C_{13}H_{20}N_2O_2S$): calculated. 268. found 269 [M+H]$^+$.

80.0 g (0.298 mol) of (1-Cyclohexyl-2-thioxo-2,3-dihydro-1H-imidazol-4-yl)-acetic acid ethyl ester, dissolved in 200 ml acetic acid, were slowly added to $H_2O_2$ in 400 ml acetic acid at 0° C. within 90 min at 10° C. After addition the cooling was removed and the mixture was allowed stirring for 1 h. The solution was carefully poured into 80 g $Na_2SO_3$ in 300 ml water and ice. The slurry was concentrated and the acidic residue was treated with saturated aqueous $K_2CO_3$ and saturated aqueous $NaHCO_3$ (pH 8). The mixture was extracted with AcOEt (1×400 ml, 2×150 ml). The combined organic layers were washed with brine, dried with $MgSO_4$, concentrated and dried under reduced pressure and gave 70.0 g (0.296 mmol, 99%) of (1-Cyclohexyl-1H-imidazol-4-yl)-acetic acid ethyl ester as a brown oil which could be used without further purification in step A of Example 1.

HPLC: $t_R$=0.77 min (YMC J' sphere ODS H 80 20×2.1 mm, 4 μm, A: $H_2O$+0.05% TFA, B: MeCN, 4%→95% B in 2 min, 1 ml/min, 30° C.);

Mass (ES+) ($C_{13}H_{20}N_2O_2$): calculated. 236. found 237 [M+H]$^+$.

The invention claimed is:
1. A process for obtaining the compound of the formula I

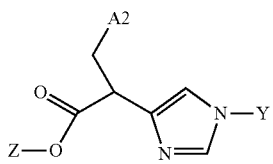 (I)

and/or all stereoisomeric forms of the compound of the formula I and/or mixtures of these forms in any ratio, where
A2 is aminopyridyl,
Y is —$(C_3-C_8)$-cycloalkyl,
and
Z is 1) —$(C_1-C_6)$-alkyl,
2) —$(C_1-C_6)$-alkyl-OH,
3) —$(C_1-C_4)$-alkylene-$(C_3-C_6)$-cycloalkyl,
4) —$CH_2$-phenyl, wherein phenyl is unsubstituted or substituted once or twice by $NO_2$ or methoxy,
5) —$CH_2$—CH=$CH_2$ or
6) —$(C_1-C_{10})$-alkylene-O—C(O)—O—$(C_3-C_6)$-cycloalkyl, which comprises
A) reacting a compound of the formula IV

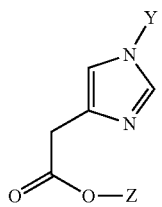 (IV)

with an oxalic acid diester of formula V in the presence of a base and a solvent

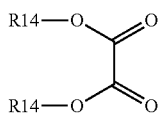 (V)

wherein R14 is —$(C_1-C_6)$-alkyl, to give a compound of formula VI

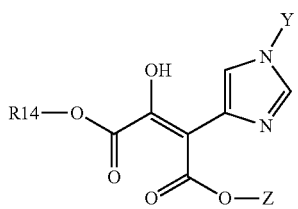 (VI)

B) reacting the compound of formula VI with the compound of formula VII in the presence of a base and a solvent, optionally in the presence of a quarternary ammonium halide catalyst:

W—$CH_2$-A2-R15 (VII)

wherein W is a halogen or a sulfonyl ester, and R15 is an amino-protecting group, to give a compound of formula VIII

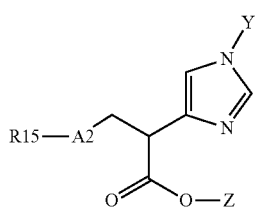 (VIII)

C) and deprotecting the compound of formula VIII in the presence of a deprotecting agent and a solvent to give a compound of formula I, or
D) optionally a compound of the formula I which has been prepared by process steps A), B) and C) and occurs owing to its chemical structure in enantiomeric forms being fractionated by salt formation with enantiopure acids or bases, chromatography on chiral stationary phases or derivatization using chiral enantiopure compounds, separation of the diastereomers obtained in this way, and elimination of the chiral auxiliary groups into the pure enantiomers.

2. Process as claimed in claim 1, wherein the formula I is prepared where A2 is 2-aminopyridyl,
Y is —$(C_3-C_8)$-cycloalkyl,
and
Z is —$(C_1-C_6)$-alkyl or benzyl.

3. The process according to claim 1 wherein Z is ethyl, $A_2$ is 6-aminopyrid-3-yl and Y is cyclohexyl.

4. The process according to claim 1 wherein R14 is ethyl.

5. The process according to claim 1 wherein said base in step A) is an alkali alkoxide base.

6. The process according to claim 5 wherein said base is sodium ethoxide.

7. The process according to claim 1 wherein said solvent in step A) is an alcohol.

8. The process according to claim 7 wherein said solvent is ethanol.

9. The process according to claim 1 wherein the compound of formula VII is (5-bromomethyl-pyridin-2-yl)-carbamic acid tert-butyl ester.

10. The process according to claim 1 wherein said base in step B) is selected from the group consisting of alkali metal amides, metal hydrides, alkoxides, amine bases, alkali metal hexamethyldisilazides and phosphazenes.

11. The process according to claim 10 wherein the base is lithium hexamethyldisilazide.

12. The process according to claim 1 wherein said solvent in step B) is selected from the group consisting of ethers and alcohols.

13. The process according to claim 12 wherein said solvent is ethanol.

14. The process according to claim 12 wherein said solvent is tetrahydrofuran.

15. The process according to claim 1 wherein said catalyst in step B) is tetra-n-butylammonium iodide.

16. The process according to claim 1 wherein step B) is done at a pH of 9.0 or greater.

17. The process according to claim 16 wherein the pH is 10.5.

18. The process according to claim 1 wherein R15 is tert-butoxycarbonyl.

19. The process according to claim 1 wherein said deprotecting step C) is done in the presence of an organic or mineral acid.

20. The process according to claim 19 wherein said mineral acid is chosen from the group from the group consisting of HBr, HCl, HI, $H_2SO_4$, and $H_3PO_4$.

21. The process according to claim 19 wherein said organic acid is chosen from the group consisting of acetic acid, trifluoromethane sulfonic acid, and triflouroacetic acid.

22. The process according to claim 21 wherein said organic acid is acetic acid.

23. The process according to claim 1 wherein said solvent in deprotecting step C) is chosen from the group consisting of ethers, alcohols and water.

24. The process according to claim 23 wherein said solvent is water.

25. The process according to claim 1 wherein said chiral enantiopure compound is an amino acid.

* * * * *